United States Patent
Turng et al.

(10) Patent No.: US 12,173,125 B2
(45) Date of Patent: Dec. 24, 2024

(54) METHODS OF MAKING POLYTETRAFLUOROETHYLENE/POLYMER COMPOSITES AND USES THEREOF

(71) Applicant: Wisconsin Alumni Research Foundation, Madison, WI (US)

(72) Inventors: Lih-Sheng Turng, Madison, WI (US); Yiyang Xu, Madison, WI (US); Dongfang Wang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1337 days.

(21) Appl. No.: 16/744,497

(22) Filed: Jan. 16, 2020

(65) Prior Publication Data

US 2021/0221961 A1 Jul. 22, 2021

(51) Int. Cl.
C08J 3/00 (2006.01)
A61K 31/618 (2006.01)
(Continued)

(52) U.S. Cl.
CPC ............ *C08J 3/005* (2013.01); *A61K 31/618* (2013.01); *A61K 47/32* (2013.01); *A61K 47/34* (2013.01); *A61L 27/16* (2013.01); *A61L 27/18* (2013.01); *A61L 27/26* (2013.01); *A61L 27/507* (2013.01); *A61L 27/54* (2013.01); *A61L 27/56* (2013.01); *A61L 27/58* (2013.01); *B29C 48/0012* (2019.02); *B29C 48/0018* (2019.02); *B29C 48/022* (2019.02); *B29C 48/023* (2019.02); *C08J 9/26* (2013.01); *C08J 9/283* (2013.01); *C08L 27/18* (2013.01); *A61L 27/48* (2013.01); *A61L 2300/414* (2013.01); *B29K 2027/18* (2013.01); *C08J 2201/046* (2013.01); *C08J 2201/0462* (2013.01); *C08J 2207/10* (2013.01); *C08J 2327/18* (2013.01); *C08J 2467/04* (2013.01); *C08J 2475/04* (2013.01); *C08L 2201/06* (2013.01); *C08L 2203/02* (2013.01)

(58) Field of Classification Search
None
See application file for complete search history.

(56) References Cited

U.S. PATENT DOCUMENTS

| 5,102,921 A | 4/1992 | Harada et al. |
| 5,891,507 A * | 4/1999 | Jayaraman .............. A61L 31/10 |
| | | 427/601 |

(Continued)

OTHER PUBLICATIONS

Ariawan ("Paste Extrusion of Polytetrafluoroethylene Fine Powder Resins", Ph.D thesis, Oct. 2001, The University of British Columbia) (Year: 2001).*

(Continued)

*Primary Examiner* — Sin J Lee
(74) *Attorney, Agent, or Firm* — Sandberg Phoenix & von Gontard, PC

(57) ABSTRACT

Methods of making polytetrafluoroethylene (PTFE)/polymer composites are disclosed herein. The products can be used in the field of bio- and medical applications, such as for use in artificial blood vessels, vascular grafts, cardiovascular and soft tissue patches, facial implants, surgical sutures, and endovascular prosthesis, and for any products known in the aerospace, electronics, fabrics, filtration, industrial and sealant arts.

15 Claims, 4 Drawing Sheets
(4 of 4 Drawing Sheet(s) Filed in Color)

(51) Int. Cl.
*A61K 47/32* (2006.01)
*A61K 47/34* (2017.01)
*A61L 27/16* (2006.01)
*A61L 27/18* (2006.01)
*A61L 27/26* (2006.01)
*A61L 27/48* (2006.01)
*A61L 27/50* (2006.01)
*A61L 27/54* (2006.01)
*A61L 27/56* (2006.01)
*A61L 27/58* (2006.01)
*B29C 48/00* (2019.01)
*B29C 48/92* (2019.01)
*C08J 9/26* (2006.01)
*C08J 9/28* (2006.01)
*C08L 27/18* (2006.01)
*B29K 27/18* (2006.01)

(56) References Cited

U.S. PATENT DOCUMENTS

| | | | |
|---|---|---|---|
| 9,446,553 B2* | 9/2016 | Humphrey | B29C 55/08 |
| 2002/0042645 A1 | 4/2002 | Shannon | |
| 2002/0111667 A1 | 8/2002 | Girton et al. | |
| 2004/0157024 A1 | 8/2004 | Colone | |
| 2004/0210306 A1* | 10/2004 | Quijano | A61F 2/2475 |
| | | | 623/2.17 |
| 2005/0256075 A1* | 11/2005 | Alitalo | A61K 38/1866 |
| | | | 514/44 R |
| 2013/0071550 A1 | 3/2013 | Edwin et al. | |
| 2017/0035548 A1 | 2/2017 | Bebb et al. | |

OTHER PUBLICATIONS

Ansari et al ("Paste Extrusion and Mechanical Properties of PTFE", International Polymer Processing, vol. 30(5) (Nov. 2015), p. 603-614) (Year: 2015).*

* cited by examiner

FIGS. 2A-2C
FIG. 2A
Water Contact Angle
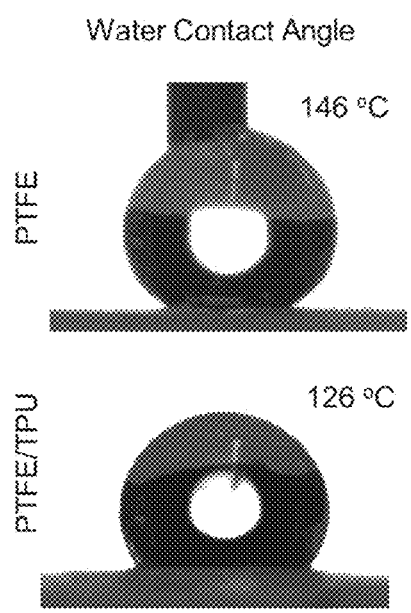
FIG. 2B
Surface Morphology
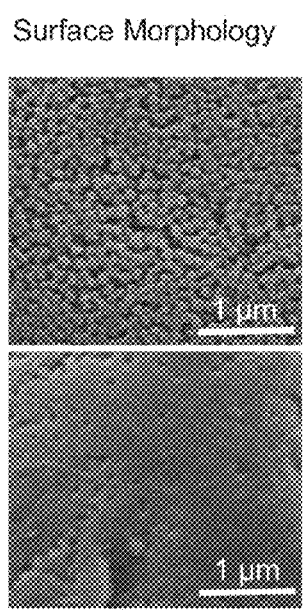
FIG. 2C
ePTFE Structure
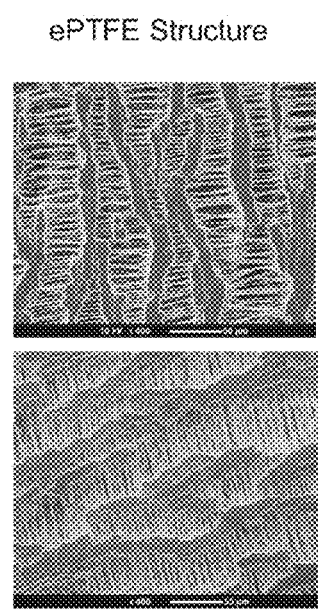
FIGS. 3A-3C
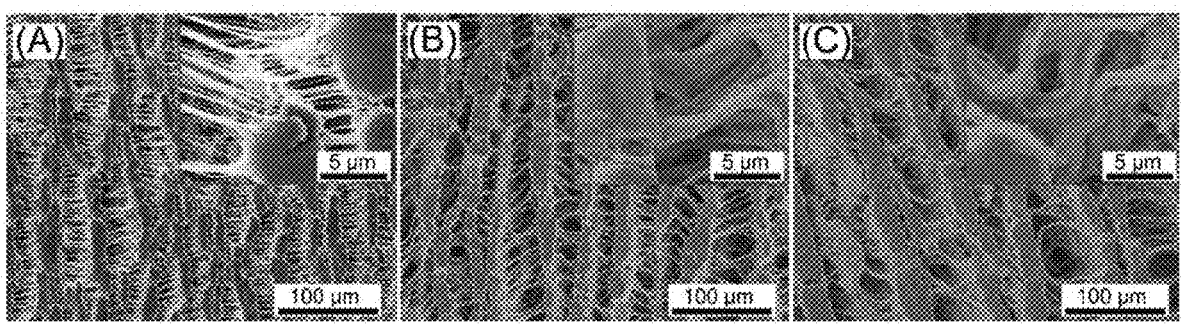

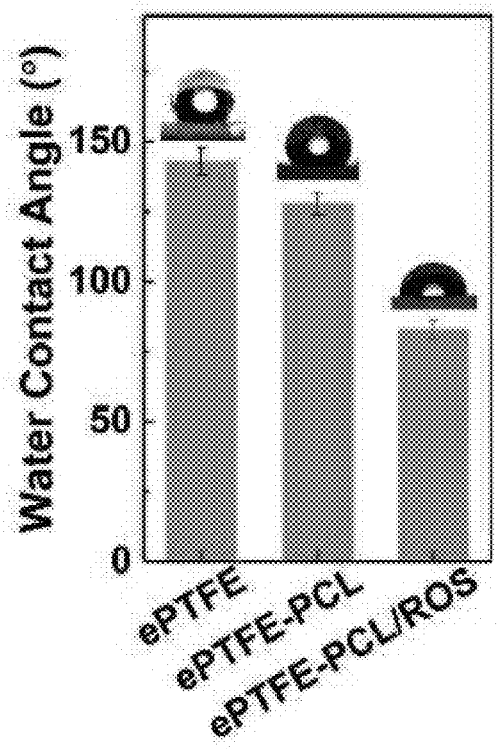
FIG 4 Wettability
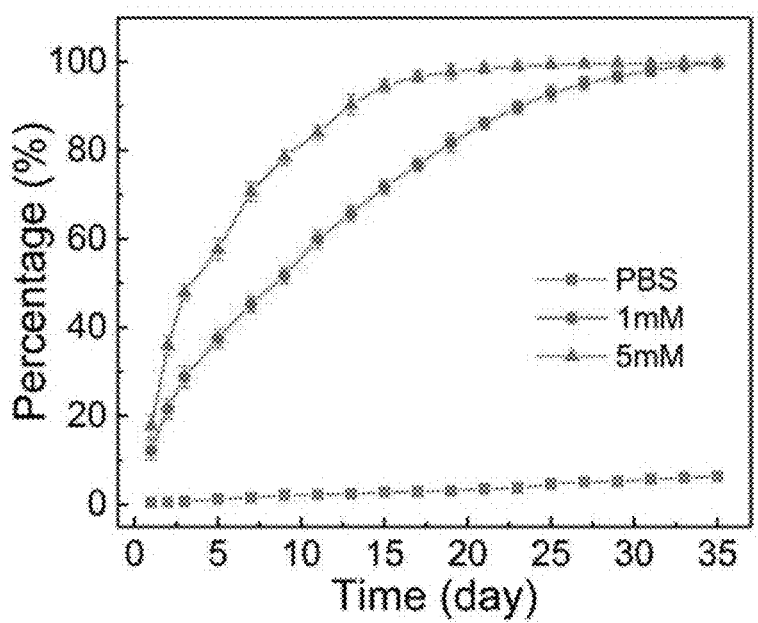
FIG 5 Drug release

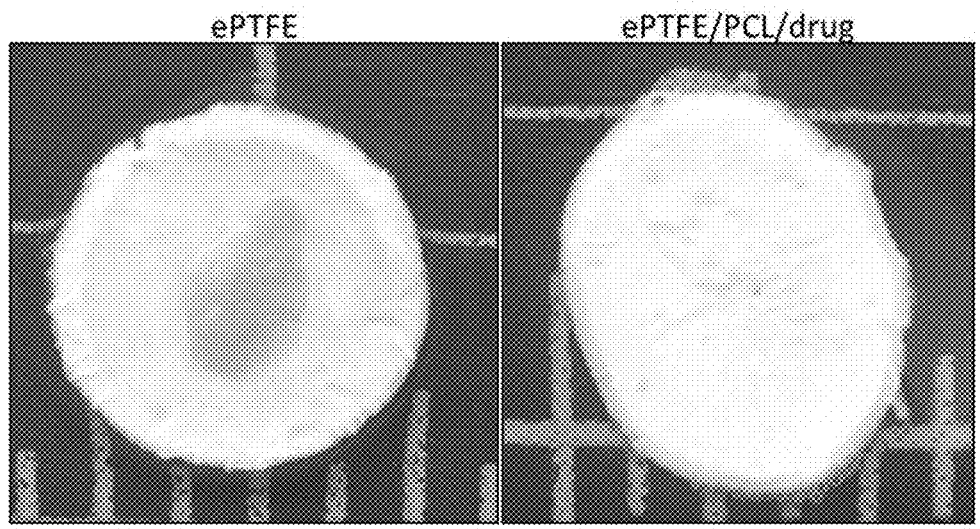

METHODS OF MAKING POLYTETRAFLUOROETHYLENE/POLYMER COMPOSITES AND USES THEREOF

STATEMENT OF GOVERNMENT SUPPORT

This invention was made with government support under U01HL134655 awarded by the National Institutes of Health. The government has certain rights in the invention.

BACKGROUND OF THE DISCLOSURE

The present disclosure relates generally to methods of making polytetrafluoroethylene (PTFE)/polymer composites. Polytetrafluoroethylene (PTFE) possesses a number of special properties such as a low dielectric constant (i.e., good electrical insulator), high thermal resistance, low coefficient of friction, low flammability, resistance to UV light, hydrophobicity, oleophobicity, and chemical inertness. Expanded polytetrafluoroethylene (ePTFE) possesses other attractive attributes such as porosity, air permeability and tunable strength. Due to its biocompatibility and inertness, ePTFE has also been particularly useful in the field of bio- and medical applications, such as for use in vascular grafts, cardiovascular and soft tissue patches, facial implants, surgical sutures, and endovascular prosthesis. As used herein, PTFE refers to PTFE, ePTFE, and their sintered counterparts.

Due to its inability to flow, even when melted, and inability to be dissolved, there is no effective method for making PTFE/polymer composites. These shortcomings limit the applications of PTFE/composites and/or require secondary processing to prepare the composites.

Accordingly, there is need to develop a method of fabricating PTFE/polymer composites. It would be further advantageous if the processing allowed for bio-functional materials to be added to the final composite products to provide additional desired functions.

BRIEF DESCRIPTION OF THE DISCLOSURE

The present disclosure is directed to methods of making PTFE/polymer composites. By blending the PTFE material with various other polymers, it has been found that the functionality of the PTFE is improved in many aspects, including biocompatibility, bioactivity, hydrophilicity and surface roughness. Additionally, the processing methods of the present disclosure allow modification of the products through the addition of biodegradable polymers. For example, in one embodiment, by incorporating a drug-loaded biodegradable polymer, controlled drug release can be easily achieved, making the methods of the present disclosure appealing in biomedical applications, such as artificial blood vessels, wound dressings and vascular patches.

Accordingly, in one aspect, the present disclosure is directed to processes of making a polytetrafluoroethylene (PTFE)/polymer composite product, the process including: dissolving a polymer with a solvent to form a polymer solution; immersing a PTFE material into the polymer solution; and extruding the PTFE/polymer blend into an intermediate or final product. In some embodiments, the processes further include evaporating the solvent from the PTFE/polymer solution and adding a lubricant to the PTFE/polymer blend before extruding the PTFE/polymer blend. In yet other suitable embodiments, the processes further include expanding the extruded products.

In some embodiments, a target material such as a bio-functional material, a therapeutic, a natural compound, an aesthetic agent and combinations thereof, is dissolved into the PTFE/polymer solution.

In one embodiment, the PTFE material is an extruded (and, optionally expanded) PTFE product. In this embodiment, the PTFE product can be immersed to coat the product with the additional polymer, and optionally, a target material, to provide improved properties to the extruded PTFE product. The process of this embodiment includes: dissolving a polymer with a solvent to form a polymer solution; optionally, dissolving a target material into the polymer solution; and immersing a PTFE raw material or product into the polymer solution.

In another aspect, the present disclosure is directed to a process for preparing a polytetrafluoroethylene (PTFE)/polymer foam composite product. The process includes: dissolving a polymer with a solvent to form a solvent/polymer solution; blending a PTFE material into the solution to form a blend; extruding the PTFE/polymer blend; and leaching the polymer from the blend to form pores in the PTFE/polymer composite product. In some embodiments, there are at least two polymers that are dissolved in the solvent to form the solvent/polymer solution. In these latter embodiments, the process can include leaching the first and/or second (and subsequent) polymers from the blend to form pores in the composite product.

In yet another aspect, the present disclosure is directed to an artificial blood vessel including the composite products described herein.

In yet another aspect, the present disclosure is directed to a polytetrafluoroethylene (PTFE)/polymer composite product including a PTFE material and a dissolvable polymer as prepared by the processes described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIGS. 2A-2C depict (FIG. 2A) water contact angle; (FIG. 2B) surface morphology, and (FIG. 2C) expanded structure of pure PTFE and PTFE/TPU composites.

FIGS. 3A-3C demonstrates the processabilty and expandability are not impaired. FIG. 3A depicts neat ePTFE material; FIG. 3B depicts a ePTFE/PCL composite; and FIG. 3C depicts ePTFE/PCT composite including a drug material.

FIG. 4 reveals an improved wettability, which is good for cell adhesion.

FIG. 5 shows the drug release period and 35 days is long enough for artificial blood vessel application. PBS stands for phosphate buffered saline and mM is the unit of the reactive oxygen species (ROS) drug used to test the drug release profile FIG. 6 exhibits a good anticoagulant property. The peach color indicates a blood clot (thrombus).

DETAILED DESCRIPTION

Figure 1:
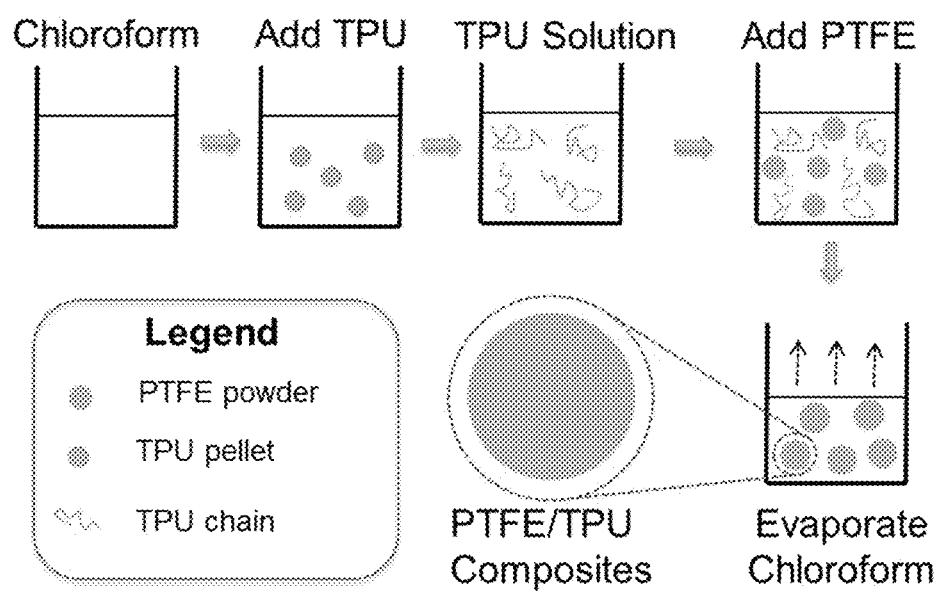
FIG. 1 depicts a schematic of a process of preparing the PTFE/polymer composite of one embodiment of the present disclosure. Chloroform is used as the solvent for the thermoplastic polyurethane polymer.

Unless defined otherwise, all technical and scientific terms used herein have the same meaning as commonly understood by one of ordinary skill in the art to which the disclosure belongs.

Currently, however, PTFE is primarily used as a filler in composite materials as PTFE cannot be dissolved by organic solvents and cannot flow even when melted. The methods of the present disclosure provide an easy efficient means to prepare PTFE/polymer composites (i.e., PTFE as the matrix material) with any dissolvable polymer without impairing the processability of the PTFE/polymer composites. Additionally, the methods of the present disclosure allow the PTFE/polymer and ePTFE/polymer composite products to be further modified with added functional target materials (e.g., bio-functional materials (also referred to herein as biomolecules)).

It has recently been found that the methods allow PTFE to be easily coated with any dissolvable polymer to form a PTFE/polymer composite having desired functional propertie(s). As used herein, "coated" or "coating" or "coat" refers to the dissolvable polymer permeating, penetrating, diffusing, and/or distributing through the PTFE material; that is, the polymer passes through pores, spaces, gaps and any other interstices of the PTFE material.

Generally, the methods initially include dissolving a target polymer into a solvent. Any dissolvable polymer is suitable for use in the methods of the present disclosure. Exemplary polymers include polylactic acid (PLA), polycaprolactone (PCL), thermoplastic polyurethane (TPU), polyvinyl alcohol (PVA), poly(ethylene oxide) (PEO) (also, known as poly (ethylene glycol) (PEG)), polycarbonate (PC), polystyrene (PS), polyamide (PA, also known as nylon), polyacrylonitrile (PAN), and the like, and combinations thereof. The polymers for use in the PTFE/polymer composites provide functional and structural benefits to the compositions. By way of example, when the biodegradable PLA or PCL is used as the polymer, the composite can be loaded with a drug or other therapeutic such to allow for a PLA/drug of PCL/drug coating on PTFE powders to slowly release the drug as the PLA or PCL biodegrades into harmless byproducts. This use of the composites allows for controllable sustained release of the drug such as when used as ePTFE artificial blood vessels.

The dissolvable polymer is dissolved in a solvent. Solvents such as biocompatible lower alkyl ($C_1$-$C_{10}$) alcohols (e.g., methanol, ethanol, isopropanol, and the like), or organic solvents such as ketones (e.g., acetone), methyl chloride (e.g., dichloromethane, and chloroform), furan (e.g., tetrahydrofuran), amide (e.g., dimethylformamide), and dimethyl sulfoxide can behave as dual purpose solvents (that is, solvents for dissolving target polymers and as lubricants for extrusion of the resulting polymer composite blends into final products). For example, these solvents/ lubricants allow for good wettability on PTFE powders and are fast and easily removed through evaporation. In contrast to traditional lubricants (e.g., Naphtha), which are flammable, polluting, toxic and have been linked to latent diseases, some biocompatible solvents and lubricants may be up to 100% non-toxic and non-corrosive, thereby further enhancing the safety and utility of finished PTFE and ePTFE/composite products.

Additional suitable solvents include other organic solvents, for example, acetic acid, ethyl acetate, acetonitrile, chloroform, benzene, methylbenzene, dimethylbenzene, acetone, 2-butanone, cyclopentanone, pentane, n-hexane, cyclohexane, heptane, dichloromethane, dichloroethane, trichloroethane, tetrachloromethane, tetrachloroethane, trimethylpentane, 1,4-dioxane, chloroform, ether, dimethyl sulfoxide (DMSO), dimethylformamide (DMF), tetrahydrofuran (THF), and combinations thereof. The organic solvents can further be combined with a carrier such as water, and the like, to form a dual purpose solvent and lubricant mixture.

The dissolvable polymer is added to the solvent for a suitable time to completely dissolve the polymer. Typically, the time periods for dissolving include ranges of from about 0.5 hours to about 2 hours, using normal pressure and stirring speeds ranging from about 2 rpm to about 200 rpm. Heating may be helpful for dissolving, but the specific temperature depends on the solvent and polymer material used. Typically, however, the temperature ranges between about 50° C. to about 200° C. and should be under the boiling point of the solvent and the degradation temperature of the polymer. Suitably, the polymers may be dissolved in the solvent by stirring using any means suitable as known in the art. For example, in one embodiment, the solvent/ polymer solution is magnetically stirred to help dissolve the polymer faster.

PTFE material, typically in the form of particles and powders, is immersed into the solution including the solvent and fully-dissolved polymer to blend the PTFE material with the solution. For blending with the PTFE material, it is generally suitable for the polymer to be present in the solution in an amount of from about 0.1% to about 10% by weight of the total solution. The polymer solution and PTFE powders are blended using any means in the art for blending, and typically, are blended for a rolling time of from about 30 minutes to about 120 minutes and soaking time of from about 30 minutes to about 48 hours. Soaking is typically conducted at a temperature of 40° C. to keep the solution at a lower temperature than the boiling point of the solvent for a period of time, which facilitates uniform wetting.

In an alternative embodiment, an extruded, and optionally expanded, PTFE product may be coated with a polymer using the processes of the present disclosure. When a prepared extruded (and, optionally, expanded) PTFE product is to be coated, the process includes immersing the PTFE product into the solution as described above to uniformly coat the product with the solution.

In further embodiments, it has been advantageously found that the solvents and lubricant described herein can be used as a carrier for target materials (e.g., bio-functional materials) to allow for introduction of the biomolecules into the final extruded product. Particularly, the polytetrafluoroethylene (PTFE) powder is pretreated with a target material during the mixing of the PTFE powders with the polymer solution (with or without the addition of water). The pretreatment process generally includes: dissolving a target material in the solvent/polymer solution to form a target ternary solvent/polymer solution; and then immersing the polytetrafluoroethylene (PTFE) powder in the ternary solvent/polymer solution to form the blend, which is then preformed, and extruded and sintered (if applicable), to form a composite product including the target material.

Specifically, target materials may include bio-functional materials (e.g., dopamine, heparin, growth factors (e.g., epidermal growth factor (EGF), fibroblast growth factor (FGF), nerve growth factor (NGF), platelet-derived growth factor (PDGF), vascular endothelial growth factor (VEGF), insulin-like growth factor (IGF), granulocyte-macrophage colony-stimulating factor (GMCSF), granulocyte-colony stimulating factor (GCSF), transforming growth factor (TGF) erythropieitn (EPO), thyroperoxidase (TPO), bone morphogenetic proteins (BMP), hepatocyte growth factor (HGF), growth differentiation factors (GDF), Neurotrophins, melanocyte-specific factor (MSF), sarcoma growth factor (SGF), and the like, and combinations thereof), and the like, and combinations thereof), anticoagulants (e.g., heparin, salicin, and bivalirudin), therapeutics (e.g., anticancer agents (e.g., nimustine hydrochloride, doxifluridine, daunorubicin), anti-inflammatory agents (e.g., aspirin, cephradine, cilastatin), antibiotic agents (e.g., penicillin, cephalosporins, erythromycin), natural compounds (e.g., vitamins), aesthetic agent (e.g., pigments), and the like, and combinations thereof that can be dissolved in the solvent/polymer solution and, after the evaporation of the solvent and/or lubricant, will remain inside of the extruded product, endowing them with specific desirable biofunctional, physical and aesthetic properties.

When dissolved in the solvent/polymer solution (with or without carrier), the target materials are typically present in an amount of from about 0.1% by weight to about 10% by weight total. Advantageously, with the use of the solvents and lubricants in the present disclosure, the target material(s) can be dissolved in the solvents and lubricants at room temperature.

The target material is dissolved in the solvents and lubricants for a period of from about 0.1 hours to about 3.0 hours, suitably, from about 0.2 hours to about 2.0 hours, and more suitably, from about 0.5 hours to about 1.0 hour.

Further, dissolving conditions include dissolving at room temperature, normal pressure, and stirring at speeds ranging from about 2 rpm to about 200 rpm.

Historically, PTFE is difficult to modify because of its chemical inertness. Previous solutions for improving PTFE's behavioral properties have included surface coating, chemical bonding, and plasma treatment. Surface coating, however, cannot reach deep inside the PTFE material and resulting products. Chemical bonding requires toxic chemicals and complex procedures. And, plasma treatment is greatly limited by the resulting PTFE product's geometry. By contrast, using the methods as disclosed herein, the surface of the PTFE powders was completely coated by the polymer (and, in some embodiments, the polymer and target material). Further, as verified by subsequent expansion experiments and characterization, the polymer and the target material were evenly distributed throughout the PTFE material (see FIG. 1). And, the processability of the PTFE material was not impaired by this process, such that an expanded porous PTFE (i.e., ePTFE)/polymer composite could be produced (see FIG. 2).

As noted above, in some suitable embodiments, it is suitable to include water with the solvent to form a carrier mixture to dissolve the polymer and, in some embodiments, a target material. The addition of water (or other bio-friendly liquid) can increase the solubility of target molecules such as bio-functional materials without compromising the dissolving function of the solvent/polymer solution. Further, the higher the water ratio, the more bio-functional material the polymer solution (e.g., solvent/polymer, water) could carry. However, if the water ratio is too high, the solubility of the polymer will be impaired, which results in processing failure. Typically, when water is used with the solvent, the solvent/water mixture has a ratio of solvent:water of from about 10:90 to about 100:0, more suitably, the ratio is larger than 50:50; and even more suitably, the ratio is 70:30.

In some embodiments, once blended, the blend may be preformed at room temperature (23° C.+/−2° C.). That is, the blend is compressed and compacted with a defined pressure and compression rate. Preforming has two functions: first, it gives shape and second, it removes any air pockets from within the composite material. The maximum pressure depends on the consistence of the PTFE material, additional polymer included, and presence of any additional target materials in the blend (e.g., bio-functional materials). Typically, the pressure ranges from about 1 MPa to about 30 MPa, and suitably about 2 MPa. The pressure is typically maintained for a period of from about 0 minutes to about 120 minutes, including from about 0 to about 60 minutes.

The blend (preformed or not) is extruded through any extruder known in the extruding arts to give the final composite product its shape. In some suitable embodiments, the blend is extruded in a ram extruder.

In some embodiments, the solvent is then evaporated from the PTFE/polymer solution (alternatively, if an extruded, and optionally expanded, PTFE product is coated with a polymer using the processes of the present disclosure, the solvent is then evaporated from the extrudate) by heating or ventilating. Conventionally, to evaporate the solvent, the PTFE/polymer solution/extrudate had to be heated to a temperature of from 60° C. to about 200° C. for a period of from about 0.5 minutes to about 120 minutes. With the use of lower boiling point solvents, the process of the present disclosure can evaporate the solvent at room temperature for a period of from about 1 hour to about 96 hours, including from about 1 hour to about 72 hours. This proves beneficial as it is more cost effective and energy efficient. Further, if target molecules are introduced in the products, the lower evaporation temperature prevents degradation of some target materials (e.g., bio-functional materials) and/or their functional properties that they provide the composite products.

In some embodiments, the extruded composite product is expanded into a desired size and shape. Expansion can be at a typical expansion temperature (200-300° C.), however, it has advantageously been found that solvents used in the present disclosure such as ethanol have a lower boiling point, and thus, can be expanded at lower temperatures, for example from about 25° C. to about 340° C., including from about 25° C. to about 300° C. Further, suitable stretch rates include from about 1 mm/min to about 5000 mm/min, including from about 1 mm/min to about 1000 mm/min.

Maximum expansion will vary depending on the specific application. Typically, however, maximum expansion ratios of the PTFE/polymer composite products are about 800%, more typically, the expansion ratio is from about 100% to about 800%, and more typically still, about 400%. It has been found, that PTFE tubes prepared and expanded using the processes of the present disclosure show a rough surface when the expansion ratio is larger than 400%.

By using the methods of the present disclosure, PTFE/polymer composite products are prepared to have improved functional properties, such as biocompatibility, bioactivity, hydrophilicity and surface roughness. The composite product typically includes a PTFE material and a dissolvable polymer as described herein. As noted above, PTFE has historically been used as a (minor phase) filler for composites. Alternatively, it has been known to chemically treat, coat, or graft other polymers to the surface of PTFE products, however, the content of the grafted polymer is low. The PTFE/polymer composite product of the present disclosure can be prepared with a greater content of dissolvable polymer, including from about 1 wt % to about 50 wt % or greater, and including having greater than 10 wt % to about 50 wt % of the dissolvable polymer, including from about 10 wt % to about 20 wt % of the dissolvable polymer.

The PTFE/polymer composite products can further include other target materials such as is described herein to provide improved functional and aesthetic properties.

In some embodiments, the composite product is formed as a foam. In these embodiments, a polymer is dissolved with the solvent to form the solvent/polymer solution, and after blending and extruding as described above, the polymer (also referred to herein as the sacrificial polymer) is leached from the blend to create voids/pores within the composite product. In some embodiments, more than one polymer can be used in the solvent/polymer solution. For example, a first polymer and a second polymer can be dissolved with the solvent to form the solvent/polymer solution. Then, one or both of the polymers can be leached from the blend. In some embodiments, when more than one polymer is used, the first and second polymers are the same polymers and are selected from the polymers described above. In other embodiments, the first and second polymers are different polymers, independently selected from the polymers described above. Particularly, any dissolvable polymer is suitable for use in the foam embodiments. Exemplary polymers include polylactic acid (PLA), polycaprolactone (PCL), thermoplastic polyurethane (TPU), polyvinyl alcohol (PVA), poly(ethylene oxide) (PEO) (also, known as poly(ethylene glycol) (PEG)), polycarbonate (PC), polystyrene (PS), polyamind (PA, also known as nylon), polyacrylonitrile (PAN), and the like, and combinations thereof. The resulting composite foam products can be used, for examples, in sports protection gear, advanced gear (e.g., anti-chemical suit), and aerospace applications (e.g., space suit).

Suitably, the PTFE/polymer composite products prepared by the processes of the present disclosure can be used for any products known in the aerospace, electronics, fabrics, filtration, industrial and sealant arts. It has been found herein that the composite products are particularly useful in medical implants and biomedical devices such as artificial blood vessels, vascular grafts, cardiovascular and soft tissue patches, facial implants, surgical sutures, and endovascular prostheses.

Further, the processes of the present disclosure have been found to be effective for drug loading. While untreated ePTFE has poor biocompatibility, drug-loaded ePTFE composites, for example, ePTFE/PCL composites, made via the processes disclosed herein, exhibit greatly enhanced biocompatibility (see FIGS. 3A-3C and 4-6 where ePTFE/PL/drug material was prepared), which could provide applications in the medical, food and other applicable industries.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Example 1

In this Example, TPU/PTFE composites were made for use in PTFE/ePTFE fabrication using the methods of the present disclosure.

8 grams of thermoplastic polyurethane (TPU) were dissolved in 40 grams dichloromethane (DCM) followed by blending with 80 grams polytetrafluoroethylene (PTFE). Then, the mixture was roll blended for 1 hour with a speed of 4 rpm (room temperature, normal atmosphere). After complete removal of DCM by evaporating, the resulting material was a TPU/PTFE composite.

Example 2

In this Example, PCL/PTFE composites were made for use in PCL/ePTFE fabrication using the methods of the present disclosure.

6 grams of polycaprolactone (PCL) were dissolved in 40 grams dichloromethane (DCM), followed by blending with 80 grams PTFE. Then, the mixture was roll blended for 1 hour with a speed of 4 rpm (room temperature, normal atmosphere). After evaporation of DCM, the resulting material was a PCL/PTFE composite.

Example 3

In this Example, a PCL/PTFE composite was prepared, drug loaded using the methods of the present disclosure.
Drug Synthesis Ethyl salicylate (ESA) (2.28 g, 13.72 mmol, 99%, Alfa Aser, USA) and triethylamine (1.389 g, 13.72 mmol) were dissolved in 60 mL of Dichloromethane dichloromethane (DCM). Oxalyl chloride (1.74 g, 13.72 mmol, 98%, Alfa Aser, USA) was dissolved in 40 mL of DCM and then was added to the above solution drop-wise in an ice-water bath with mechanical stirring. The reaction mixture was stirred at room temperature for 2 hours. Next, hexane (150 mL) was added to the solution, and the triethylamine hydrochloride was removed by filtration. After evaporation of hexane under vacuum, ethyl 2-(2-chloro-2-oxoacetoxy) benzoate was obtained as a colorless oily liquid and was used for further operations without purification. The chemical structure of the obtained ES-ROS was confirmed using NMR (JNM EX-400, JEOL, Japan). 1H NMR (400 MHZ, CDCl3): δ=1.35 (3H), 4.35 (2H), 7.29 (1H), 7.43 (1H), 7.64 (1H), 8.13 (1H).
Polycaprolactone (PCL) Coating on ePTFE Material for Drug Loading.

First, 1 gram of PCL was dissolved in 10 ml chloroform/dimethylformamide (DMF) mixture (v/v=7:3), and then 100 mg of the synthesized drug above was dissolved in the solution (w/v=0.1%). Prior to coating, an ePTFE blood vessel graft was first immersed in the above chloroform and DMF for 4 hours for cleaning. Then, the PCL/drug solution was injected into the ePTFE blood vessel graft which was afterward sealed and was placed on a shaker for 24 hours at 60 rpm and 37° C. Next, the yielding graft was placed on a rotary evaporator for drying. Eventually, PCL/drug coated the surfaces and pores of the ePTFE blood vessel grafts.

What is claimed is:
1. A process for preparing a polytetrafluoroethylene (PTFE)/polymer composite product, the process comprising: dissolving a polymer with a solvent to form a polymer solution; immersing a PTFE material into the polymer solution to uniformly coat the PTFE material with the polymer solution; evaporating the solvent from the PTFE/polymer solution by heating the PTFE/polymer solution to a temperature of from 60° C. to about 200° C. for a period of from about 0.5 minutes to about 120 minutes to form a PTFE/polymer blend; adding a lubricant to the PTFE/polymer blend; and extruding the PTFE/polymer blend.

2. The process as set forth in claim 1, wherein the solvent is a biocompatible lower alkyl ($C_1$-$C_{10}$) alcohol selected from the group consisting of methanol, ethanol, isopropanol, and combinations thereof.

3. The process as set forth in claim 1, wherein the solvent is selected from the group consisting of acetic acid, ethyl acetate, acetonitrile, chloroform, benzene, methylbenzene, dimethylbenzene, acetone, 2-butanone, cyclopentanone, pentane, n-hexane, cyclohexane, heptane, dichloromethane, dichloroethane, trichloroethane, tetrachloromethane, tetrachloroethane, trimethylpentane, 1,4-dioxane, ether, dimethyl sulfoxide (DMSO), dimethylformamide (DMF), tetrahydrofuran (THF), and combinations thereof.

4. The process as set forth in claim 1, wherein the polymer is selected from the group consisting of polylactic acid (PLA), polycaprolactone (PCL), thermoplastic polyurethane (TPU), polyvinyl alcohol (PVA), poly(ethylene oxide) (PEO), polycarbonate (PC), polystyrene (PS), polyamide (PA), polyacrylonitrile (PAN), and combinations thereof.

5. The process as set forth in claim 1, wherein the lubricant is the same as the solvent.

6. The process as set forth in claim 1, wherein the solvent is further mixed with water before dissolving the polymer and the solvent/water mixture has a weight ratio of 70:30.

7. The process as set forth in claim 1, wherein immersing the PTFE material comprises roll blending the PTFE material and the polymer solution for a period of from about 30 minutes to about 120 minutes.

8. The process as set forth in claim 7 further comprising soaking the blend for a period of from about 30 minutes to about 48 hours after rolling.

9. The process as set forth in claim 1 further comprising preforming the PTFE/polymer blend and extruding the preformed blend to form an extruded composite product.

10. The process as set forth in claim 9 comprising preforming the PTFE/polymer blend at a pressure of from about 1 MPa to about 30 MPa.

11. The process as set forth in claim 1 further comprising expanding the extruded product.

12. The process as set forth in claim 11, wherein the expanding is conducted at a temperature of from about 25° C. to about 340° C.

13. The process as set forth in claim 11, wherein the extruded product is expanded at a rate of from about 1 mm/min to about 1000 mm/min.

14. The process as set forth in claim 11, wherein the extruded product is expanded at an expansion ratio of from about 100% to about 800%.

15. The process as set forth in claim 1 further comprising dissolving a target material in the polymer solution.

* * * * *